(12) United States Patent
Xie et al.

(10) Patent No.: US 9,638,556 B2
(45) Date of Patent: May 2, 2017

(54) COMPACT MICROWAVE WATER-CONDUCTIVITY PROBE WITH INTEGRAL SECOND PRESSURE BARRIER

(71) Applicant: SCHLUMBERGER TECHNOLOGY CORPORATION, Sugar Land, TX (US)

(72) Inventors: Cheng-Gang Xie, The Azure (SG); Guillaume Jolivet, Singapore (SG); Renke Tang, Bergen (NO); Alexander Tuborg Vilstrup, Bergen (NO); Yngve Boee, Bergen (NO); Rolf Rustad, Radal (NO)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 14/971,028

(22) Filed: Dec. 16, 2015

(65) Prior Publication Data
US 2016/0169720 A1    Jun. 16, 2016

Related U.S. Application Data

(60) Provisional application No. 62/092,260, filed on Dec. 16, 2014.

(51) Int. Cl.
*G01F 1/58* (2006.01)
*G01F 1/74* (2006.01)
*G01N 22/00* (2006.01)

(52) U.S. Cl.
CPC ............... *G01F 1/582* (2013.01); *G01F 1/74* (2013.01); *G01N 22/00* (2013.01)

(58) Field of Classification Search
CPC ... G01F 1/58; G01F 15/00; G01F 1/38; G01F 1/56
USPC ............... 73/861.11, 861.77, 861.47, 861.08
See application file for complete search history.

(56) References Cited

U.S. PATENT DOCUMENTS

| | | | |
|---|---|---|---|
| 4,196,384 A | | 4/1980 | Schittek et al. |
| 4,599,906 A | * | 7/1986 | Freud .................... G01L 9/0073 73/706 |
| 4,790,195 A | * | 12/1988 | Feller ........................ G01F 1/10 73/861.08 |
| 5,473,256 A | | 12/1995 | Stafford et al. |
| 6,831,470 B2 | | 12/2004 | Xie et al. |
| 8,536,883 B2 | | 9/2013 | Xie et al. |
| 2003/0201842 A1 | | 10/2003 | Gard |
| 2006/0225499 A1 | | 10/2006 | Gravel et al. |

(Continued)

FOREIGN PATENT DOCUMENTS

DE       102009020439 A1    11/2010
GB             922709 A      4/1963

OTHER PUBLICATIONS

Search and Examination Report issued in related GB application GB1522241.7 on Jun. 2, 2016, 7 pages.

*Primary Examiner* — Jewel V Thompson
(74) *Attorney, Agent, or Firm* — Cameron R. Sneddon (57) ABSTRACT

Methods and devices for measuring fluid properties include an electromagnetic sensor. The electromagnetic sensor includes a coaxial probe body having a first integral pressure barrier and a second integral pressure barrier formed from coaxial-feedthrough connector. The first integral pressure barrier and the second integral pressure barrier have a desired characteristic impedance.

20 Claims, 6 Drawing Sheets

(56) References Cited

U.S. PATENT DOCUMENTS

2010/0064820 A1 3/2010 David et al.
2013/0327154 A1 12/2013 Xie et al.

* cited by examiner

COMPACT MICROWAVE WATER-CONDUCTIVITY PROBE WITH INTEGRAL SECOND PRESSURE BARRIER

CROSS-REFERENCE TO RELATED APPLICATIONS

This application claims priority to U.S. Provisional Patent Application Ser. No. 62/092,260, filed Dec. 16, 2014, which is herein incorporated by reference.

BACKGROUND

Field

This disclosure relates to multiphase flow measurement devices and more particularly to multiphase-flow water conductivity probes that may be used standalone or with multiphase flow meters.

Description of the Related Art

Wells are generally drilled into subsurface rocks to access fluids, such as hydrocarbons, stored in subterranean formations. The subterranean fluids can be produced from these wells through known techniques. Operators may want to know certain characteristics of produced fluids to facilitate efficient and economic exploration and production. For example, operators may want to know flow rates of produced fluids. These produced fluids are often multiphase fluids (e.g., those having some combination of water, oil, and gas), making measurement of the flow rates more complex.

Various systems can be used to determine flow rates for multiphase fluids. In some systems, multiphase fluids are separated into their constituent phases and these phases are then individually tested to determine flow rates. Other systems include multiphase flow meters that can be used to measure flow rates of multiphase fluids without separation. These multiphase flow meters may be smaller and lighter than traditional separators and test units, and the ability to measure flow rates without separation may be desirable in some instances. Both the traditional separator systems and the multiphase flow meter systems can also be used to determine certain other fluid characteristics of interest.

It is also desirable to determine properties of the multiphase mixture, such as the presence, fraction, and salinity of water in the mixture, as this provides information about produced and/or injected water in the mixture, about the (subsea) flow-assurance measures needed to prevent hydrate formation and/or pipeline corrosion, and may affect other measurements being made on the multiphase mixture. Microwave sensors for water-conductivity detection of multiphase flows have been used with multiphase flow meters to determine water salinity, water fraction, and water-in-liquid-ratio (WLR or water-cut).

The use of electromagnetic methods, such as microwaves, has been suggested because of their high measurement sensitivity to the presence of the water phase in a multiphase flow (water permittivity/conductivity is much higher than the permittivity/conductivity of the hydrocarbon oil-gas phases). For example, U.S. Pat. No. 6,831,470, assigned to Schlumberger, shows that the fluid-contacting front-end of a microwave open-ended coaxial probe has a pressure-integrity glass-to-metal seal acting as a first pressure barrier. The back-end of the probe may have an integral N-type connector of 50-ohm characteristic impedance. The measurement probe front-aperture is mounted flush with the pipe wall of a measurement pipe section. The probe is connected through the N-type connector to the microwave electronics housed in an explosion-proof enclosure by the use of a short microwave coaxial cable/adaptor with no pressure barrier. A bulky and sometimes expensive enclosure is needed as a second pressure barrier to contain the process fluids in case the pressure-barrier formed by the probe's glass-to-metal seal fails.

SUMMARY

Certain aspects of some embodiments disclosed herein are set forth below. It should be understood that these aspects are presented merely to provide the reader with a brief summary of certain forms the embodiments might take and that these aspects are not intended to limit the scope of the disclosure. Indeed, the disclosure may encompass a variety of aspects that may not be set forth below.

In some embodiments, an electromagnetic sensor for multiphase flow measurement includes a coaxial probe body having a passageway, a first integral pressure barrier coupled to at least a portion of the passageway, the first integral pressure barrier having a desired characteristic impedance and a second integral pressure barrier coupled to at least another portion of the passageway, the second integral pressure barrier having a desired characteristic impedance.

In some embodiments, a water conductivity probe includes a coaxial probe body having a front-aperture in which an insulator surrounds and is sealingly coupled with an inner-conductor, the inner-conductor having a first end and a second end. The insulator is sealingly coupled with an inner portion of the coaxial probe body to form first seal comprising a first integral pressure barrier. The water conductivity probe also includes an interchangeable second integral pressure barrier having a desired characteristic impedance.

In some embodiments, a water conductivity probe includes a coaxial probe body having a first integral pressure barrier and an interchangeable second integral pressure barrier.

BRIEF DESCRIPTION OF THE DRAWINGS

So that the manner in which the above recited features can be understood in detail, a more particular understanding may be had when the following detailed description is read with reference to certain embodiments, some of which are illustrated in the appended drawings in which like characters represent like parts throughout the drawings. It is to be noted, however, that the appended drawings illustrate only some embodiments and are therefore not to be considered limiting of its scope, and may admit to other equally effective embodiments.

DETAILED DESCRIPTION

In the following description, numerous details are set forth to provide an understanding of the present disclosure. It will be understood by those skilled in the art, however, that the embodiments of the present disclosure may be practiced without these details and that numerous variations or modifications from the described embodiments may be possible.

In the specification and appended claims: the terms "connect", "connection", "connected", in connection with", and "connecting" are used to mean in direct connection with" or in connection with via one or more elements"; and the term "set" is used to mean one element" or "more than one element". Further, the terms "couple", "coupling", "coupled", "coupled together", and "coupled with" are used to mean "directly coupled together" or "coupled together via one or more elements". As used herein, the terms "up" and "down", "upper" and "lower", "upwardly" and "downwardly", "upstream" and "downstream"; "above" and "below"; and other like terms indicating relative positions above or below a given point or element are used in this description to more clearly describe some embodiments of the disclosure.

Figure 1:
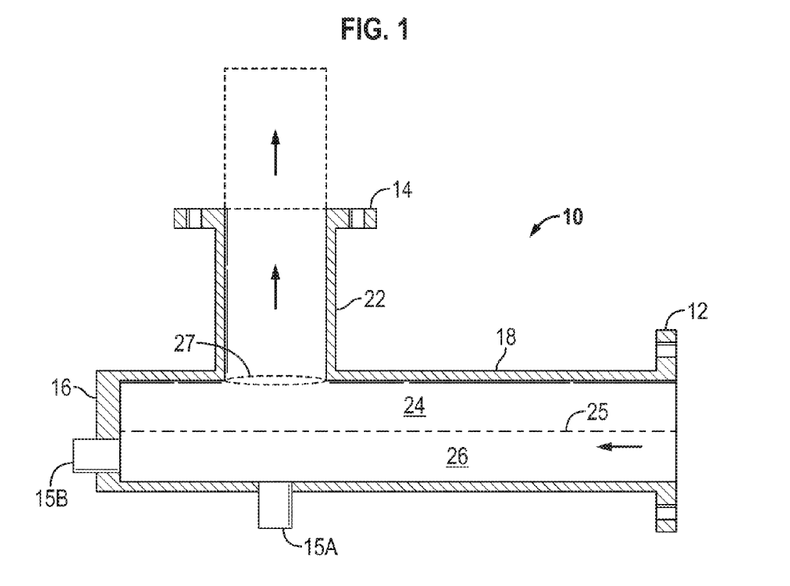
FIG. 1 shows sensor system for determining liquid properties (water conductivity/salinity, water volume fraction and/or water liquid ratio) of a multiphase mixture flowing through a blind-tee conduit, in accordance with some embodiments of the disclosure.

Electromagnetic sensors, such as microwave open-ended coaxial probes, for water-conductivity detection of multiphase flows have been used with multiphase flow meters to determine water salinity, water fraction, and water-in-liquid-ratio (WLR or water-cut). To improve the detectability of the onset of first water and changes in the water conductivity (salinity), it has been discovered through multiphase-flow experimental studies that an electromagnetic microwave sensor or sensor(s) should be installed in the liquid-rich locations of a blind-tee inlet arrangement (FIG. 1). A blind-tee inlet is often used as a flow-mixing pipework for a vertically-installed multiphase flowmeter, such as a Venturi and multi-energy gamma-ray measurement section of a dual energy multiphase flow meter.

FIG. 1 illustrates a system for determining liquid properties (water conductivity/salinity, water volume fraction and/or water liquid ratio WLR) of a multiphase mixture flowing through a conduit, in accordance with some embodiments of the disclosure. The liquid properties measuring system comprises a blind tee 10 and one or more electromagnetic sensors 15.

The blind tee 10 comprises an inlet 12, a first conduit, 18, an outlet 14, an end section 16 and a second conduit 22. In use, the multiphase mixture flows into the blind tee 10 through the inlet 12, along the first conduit 18, through the second conduit 22 and out through the outlet 14. The end section 16 acts as a flow conditioner that forces the conditioned flow of the multiphase mixture into the second conduit 22. In general, the blind tee 10 is configured so that the first conduit 18 is approximately horizontal and the second conduit 22 is approximately vertical. In embodiments of the present disclosure, the horizontal orientation of the first conduit provides that a bottom section 26 of the first conduit 18 is liquid rich and an upper section 24 of the first conduit 18 is gas rich. In some aspects, the second conduit 22 may not be arranged vertically upwards, but may be arranged vertically downwards, or at various angles with respect to the first conduit 18.

As described with respect to FIG. 1, it has been found that even in multiphase flows with high gas-to-liquid ratios (i.e., wet gas with gas volume fraction GVF>95%), liquid rich regions are produced in the bottom section 26. In some aspects, it has been found that liquid rich regions are produced in the blind tee 10 proximal to the end section 16 and/or beneath an opening 27 of the second conduit 22.

In some embodiments, one or more electromagnetic sensors 15 may be disposed below a central axis 25 of the first conduit 18. For example, the electromagnetic sensor 15A may be disposed in the bottom section 26 directly below the opening 27. Alternatively or in combination with the previous arrangement, the electromagnetic sensor 15B may be coupled with the end section 16. In some embodiments one or more of the electromagnetic sensors 15 may be disposed on the underside of the first conduit 18, in the bottom section 26 and/or coupled with the end section 16 below the central axis 25. In some embodiments a temperature sensor (not shown) may be disposed on the underside of the first conduit 18, in the bottom section 26, or coupled with the end section 16 below the central axis 25, to measure the temperature of the liquid. Flow loop test results indicate the viability of both sensor locations for first-water and/or water-conductivity change detection.

Positioning of the electromagnetic sensor(s) 15 in the manner described herein in the blind tee 10 provides for interrogation of the liquid phase of the multiphase mixture and hence for determination of the properties (water conductivity/salinity, water volume fraction and/or WLR) of the liquid phase. To measure the properties of gas (e.g., permittivity change with pressure and/or temperature), one or more of the electromagnetic sensors 15 may be disposed on the topside of the first conduit 18, in the upper section 24 above the central axis 25, near the inlet section 12. The liquid-rich locations of a blind-tee inlet, improve the detectability of the onset of first water and changes in the water conductivity which data may be used to help determine water salinity.

Figure 2:
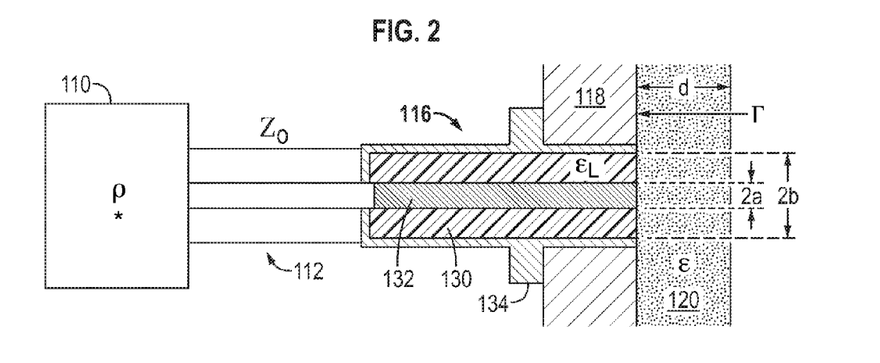
FIG. 2 shows an electromagnetic sensor installed in a pipe wall, according to some embodiments of the disclosure.

FIG. 2 shows an electromagnetic sensor, such as a coaxial probe 116, installed in a pipe wall 118. A single microwave open-ended coaxial probe 116 is flush mounted at the pipe wall 118, in contact with a (water-oil) liquid layer 120 which may have entrained gas as shown in this example. The inner conductor 132 of the probe 116 has an outer radius a and its outer conductor 134 has an inner radius b. The probe insulator 130 (which is thermally and electrically stable, preferably ceramics or glass) has a dielectric constant $\in_L$. The appropriate choice of a, b and $\in_L$ determines the characteristic impedance $Z_o$ (such as 50Ω) of probe 116, according to Equation 1:

$$Z_o = 60/(\in_L)^{1/2} \times \ln(b/a) \tag{1}$$

The probe 116 is connected to a microwave reflectometer 110 by a microwave coaxial cable 112 preferably having the same characteristic impedance $Z_o$. The microwave reflectometer 110 yields measurement of complex reflection coefficient ρ which is related to complex reflection coefficient Γ at the probe aperture.

Figure 3A:
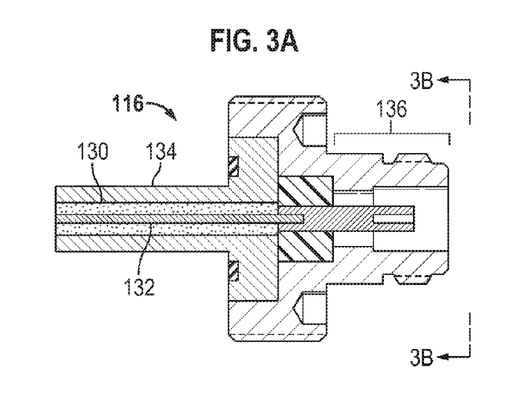
FIGS. 3A and 3B show a cross-sectional view and an isometric view of an electromagnetic sensor according to some embodiments of the disclosure.
Figure 3B:
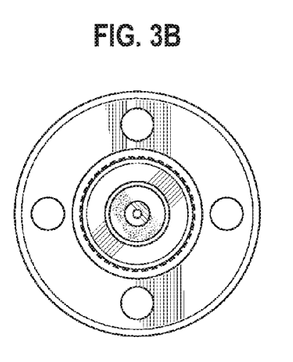

FIGS. 3A and 3B show further detail of an open-coaxial reflection probe 116. Borosilicate 7070 (glass) may be used as the insulator 130 for probe 116. Tungsten or Inconel may be used for the inner conductor 132. Inconel may be used for the outer conductor 134. Connector 136 is of N type, though other types of connectors may be used as discussed hereafter. FIG. 3B is another view from the connector side of probe 116 as shown along lines 3B in FIG. 3A.

In some applications a long microwave cable interconnects the probe and the microwave electronics, which are housed in an explosion proof enclosure to provide a second pressure barrier, for example a cylindrical protective tubing that surrounds the microwave cables leading from the probe to the microwave electronics and a cylindrical pressure-containing enclosure surrounding the microwave electronics which provides the second pressure barrier.

It may be desirable, however, to have a compact microwave open-coaxial probe which integrates a mate-able pressure-containing coaxial feedthrough connector with a short effective cable length, thereby providing small insertion loss and small thermal-induced phase drift while also maintaining a desired characteristic impedance (such as 50-Ohm) at one or more desired operating frequencies, such as 1 to 6 GHz. The microwave sensing electronics may have a short, phase-stable interconnecting cable to the microwave probe's feedthrough connector when compared to some applications. The size constraint of an explosion proof enclosure (the second pressure barrier) which may house the microwave sensing electronics, sometimes referred to as an Ex-d enclosure, can thereby be reduced along with associated costs. The probe may have a maximum allowable working pressure (MAWP) rating of 5-20 kpsi when used with a multiphase flow meter, for example 10 kpsi or 15 kpsi. This may be achieved by providing a microwave probe having a first and a second integral pressure barrier having a desired characteristic impedance.

Figure 4A:
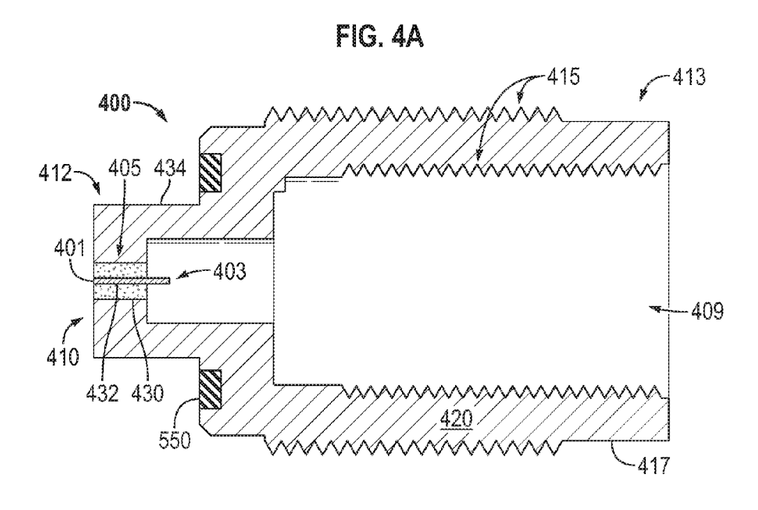
FIGS. 4A and 4B show a cross-sectional view of an electromagnetic sensor mount with a glass-to-metal seal and with a ceramic-to-metal seal, respectively, without an integral second pressure barrier.
Figure 4B:
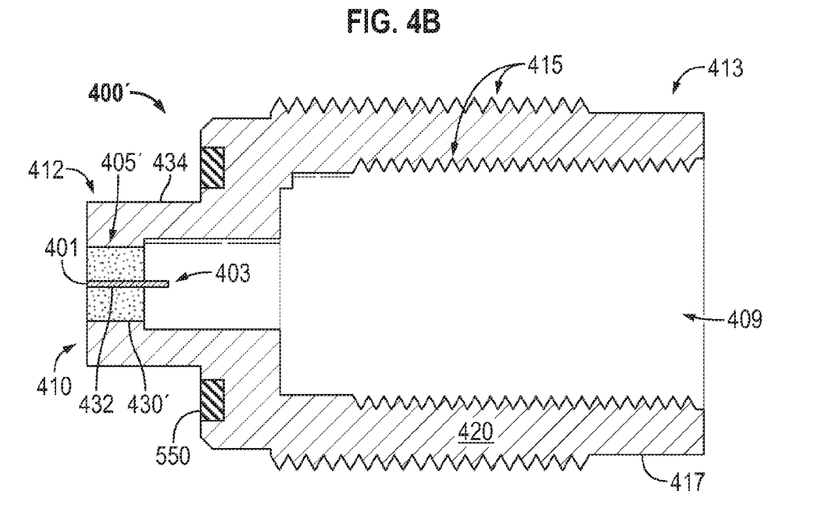

FIGS. 4A and 4B show an electromagnetic sensor, such as a microwave coaxial probe 400, 400', having a probe body 420 including a passageway 409 formed between a first probe end 412 and a second probe end 413. The first probe end 412 may include an aperture 410 that opens up to passageway 409. The probe body 420 also includes a threaded mount connection 415 for coupling with a pipe wall, though other means of coupling the probe body 420 to a pipe wall may be used. FIGS. 4A and 4B show probes 400, 400' without the integral second pressure barrier. Each type of coaxial probe, 400, 400', however, will have a first and a second pressure barrier integral with the coaxial probes 400, 400' as shown in FIGS. 4B and 5B and explained in more detail hereafter.

Figure 5A:
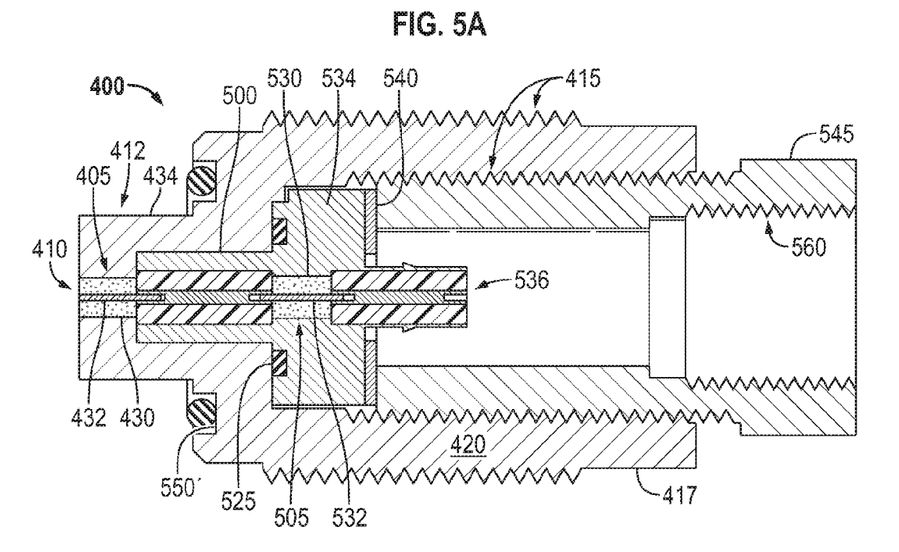
FIGS. 5A and 5B show a cross-sectional view of an electromagnetic sensor with an integral pressure-containing coaxial feedthrough connector as a second pressure barrier, using glass-to-metal seals and ceramic-to-metal seals, respectively.
Figure 5B:
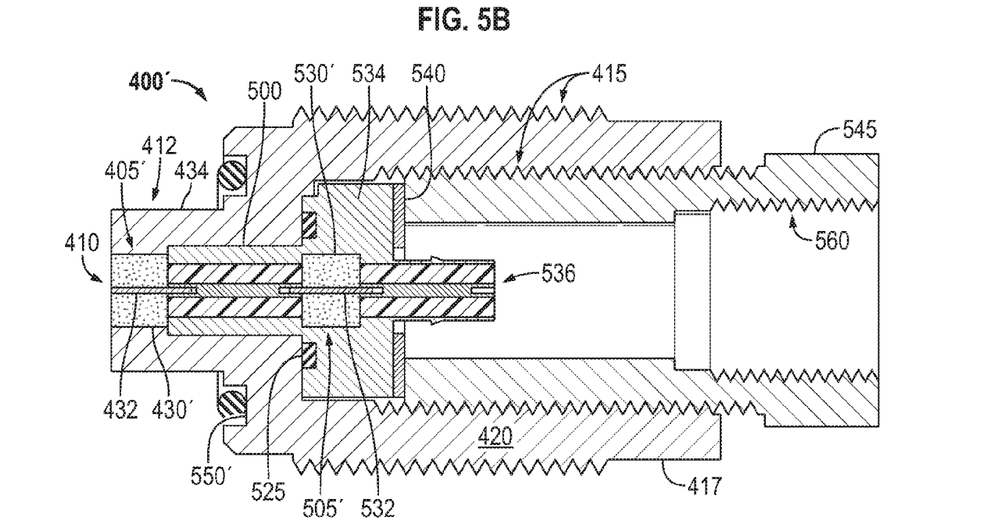

FIGS. 4A and 5A illustrate an electromagnetic sensor, such as coaxial probe 400, with a glass-to-metal seal 405 where the insulator 430 is made of glass. FIGS. 4B and 5B illustrate an electromagnetic sensor, such as coaxial probe 400', that may have an insulator 430' formed from another type of material more resistant than glass to oilfield chemical attack. A ceramic material, such as alumina, may provide a more chemical resistant material. Probe 400' shown in FIGS. 4B and 5B has an insulator 430' made of ceramic, thereby forming a ceramic-to-metal seal 405'. Other suitable materials for the insulator 430, 430' may be made from thermoplastics, such as PEEK.

Inner conductor 432 has an aperture (first) end 401 and a non-aperture (second) end 403. A first seal 405, 405' acts as the first pressure barrier in probes 400, 400'. The first seal may be the glass-to-metal seal 405 formed between insulator 430 and the inner conductor 432 and the outer conductor 434 of the open ended coaxial probe, as shown in FIG. 4A, or the ceramic-to-metal seal 405' formed between insulator 430' and inner conductor 432 and outer conductor 434, as shown in FIG. 4B. The probe design parameters (a, b and $\in_L$, FIG. 2) of the first seal 405, 405' are chosen to achieve the desired characteristic impedance (such as 50-Ohm). The first seal 405, 405' is flush with the surface of open aperture 410 of the coaxial probe 400, 400'. The insulator 430 or 430' used to form the first seal 405, 405' may be formed from any appropriate type of material that withstands the oilfield working environment and may be resistant to oilfield chemical attack while also providing insulator properties.

To keep interchangeability between the probes 400, 400' and the feedthroughs of different sealing and insulating materials while retaining the same desired characteristic impedance to minimize undesirable signal reflections at their inter-connections, the probes' design parameter a may be kept the same while the design parameter b will be different due to the differences between the dielectric-constant of the selected insulating-seal material, e.g. $\in_L \cong 4.6$ for borosilicate glass vs. $\in_L \cong 9.1$ for alumina ceramic. The outer-radius b of a ceramic-seal will hence be larger than that of a glass-seal (see FIGS. 4B and 4A, FIGS. 5B and 5A). Shrink fit and/or appropriate brazing materials can be used to form an effective ceramic-to-metal seal against oilfield high pressure and high temperature environments.

Figure 6A:
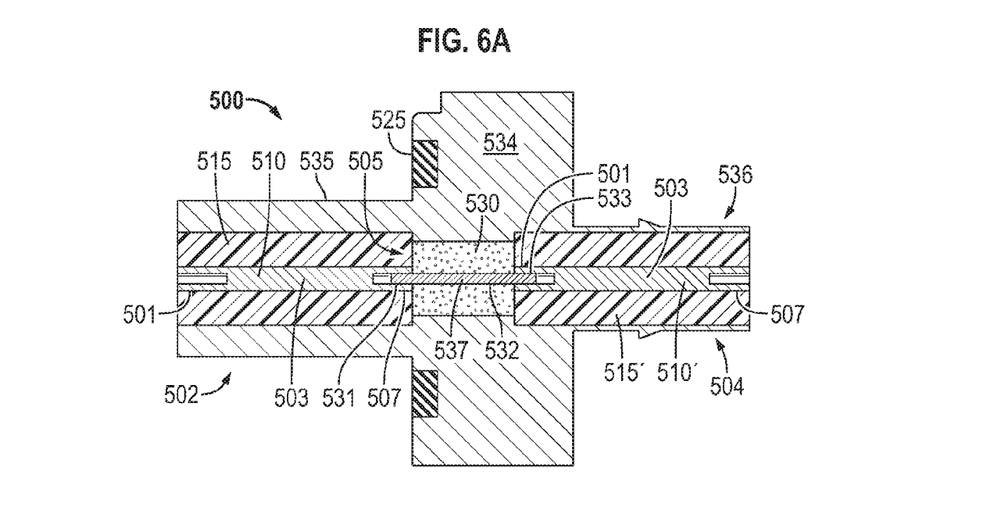
FIGS. 6A, 6B, and 6C show a cross-sectional view of an integral pressure-containing coaxial feedthrough connector as a second pressure barrier according to some embodiments of the disclosure.
Figure 6B:
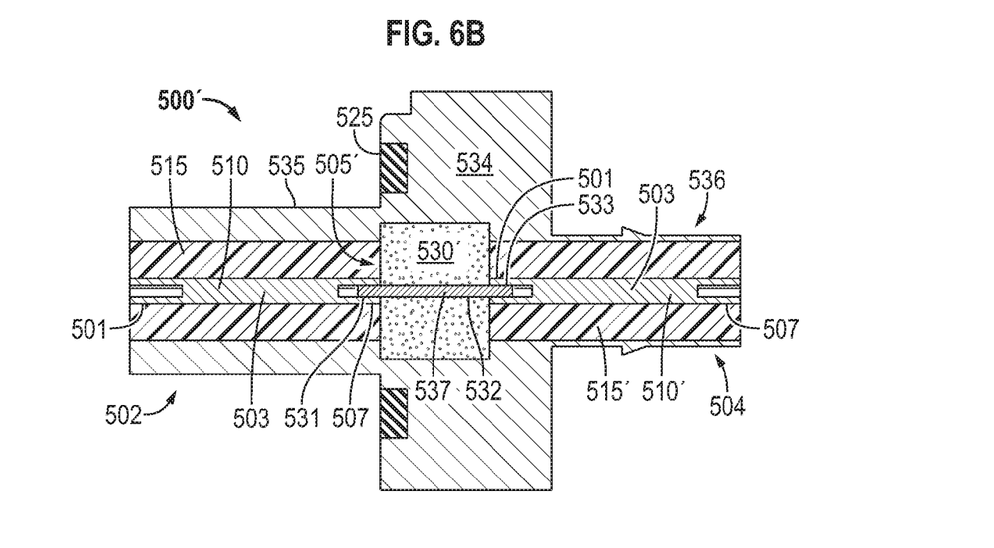

FIGS. 5A and 5B show a microwave probe 400, 400' with an integral pressure-containing coaxial feedthrough connector 500, 500' having a desired characteristic impedance and providing a second pressure barrier. FIGS. 6A and 6B show in more detail the electrical coaxial feedthrough connector 500, 500'. The coaxial feedthrough connector 500, 500' has a coaxial feedthrough connector body or housing 535 having a first end 502 and a second end 504. The coaxial feedthrough connector housing 535 may also serve as an outer conductor. In some embodiments, the feedthrough housing 535 may include a flange section 534.

The coaxial feedthrough connector 500, 500' includes a feedthrough insulator 530, 530' surrounding a center-conductor 532 having a first end 531, a center section 537, and a second end 533. The feedthrough insulator 530, 530' is sealingly coupled with at least a portion of the center-conductor 532. The coaxial feedthrough connector housing 535 surrounds and is sealingly coupled with the feedthrough insulator 530, 530' to form a second seal 505, 505' between the center-conductor 532 and the coaxial feedthrough connector housing 535. Thus, the coaxial feedthrough 500, 500' has a second seal 505, 505' which may be formed between an insulator, such as glass 530 or ceramic 530', and an inner conductor 532 and an inside portion of the feedthrough housing 535, thereby forming a glass-to metal seal 505 in FIG. 6A or a ceramic-to-metal seal 505' in FIG. 6B. This second seal 505 or 505' serves as the second pressure barrier.

In some embodiments, a portion of the glass-metal seal 505 or ceramic-metal seal 505' may be housed within the flange 534, which may also serve as the outer conductor, and positioned adjacent to a QMA connector 536. Other RF coaxial connectors, such as an SMA or N-type connector, or the like, may also be used. The feedthrough connector 500, 500' is coupled to an inner portion of the probe body 420 with a sliding washer 540 and a coaxial feedthrough holding gland 545. Thus, the coaxial feedthrough connector 500, 500' is integrally coupled with the probe 400, 400' to provide a coaxial probe having a dual-pressure integral barrier design.

The feedthrough connector 500, 500' may also include one or more lateral center-conductors 510 and 510' each having a first end 501, center section 503, and second end 507. The center-conductors 510, 510' may be disposed within the first end 502 and the second end 504 of the coaxial feedthrough connector housing 535. Two dielectric insulators 515 and 515' surround and are sealingly coupled with at least a portion of the lateral center-conductors 510 and 510', such as the first end 501 and the second end 507. In some embodiments, the dielectric insulators 515 and 515' also surround a portion of the center-conductor 532. In some embodiments, the second seal, such as a glass-metal seal 505 or a ceramic-metal seal 505', surrounds a portion of the center-conductor 532 not surrounded by the dielectric insulators 515 and 515'. A feedthrough lateral center-conductor 510 at the first end 502 of the feedthrough housing 535 mates with the non-aperture (second) end 403 of the inner conductor 432 at a first probe end 412 (FIGS. 5A and 5B).

Thus in some embodiments, a first lateral center-conductor 510 first end 501 is electrically coupled to the inner-conductor 432 of the first integral pressure barrier and the first lateral center-conductor 510 second end 507 is electrically coupled to the center-conductor 532 of the second pressure barrier. The first dielectric insulator 515 is coupled to and surrounds at least a portion of the first lateral center-conductor 510. In some embodiments, a second lateral center-conductor 510' first end 501 is electrically coupled to the center-conductor 532 of the second integral pressure barrier and the second lateral center-conductor 510' second end 507 is positioned adjacent the RF connector 536. In these embodiments, the second lateral center-conductor 510' serves as the RF connector 536 center conductor. A second dielectric insulator 515' is coupled to and surrounds at least a portion of the second lateral center-conductor 510'.

In FIGS. 4A, 5A, 4B and 5B, the probe body 420 and/or the feedthrough housing 535 may be made of Inconel 625, such as when it's desired for the probe and/or feedthrough to be $H_2S$ resistant, stainless steel 316, Monel 500, titanium, or the like. The inner conductor 432 of the probe and the inner conductor 532 of the glass-metal seal 505 or ceramic-metal seal 505' portion of the second pressure barrier (inside the flange 534 part of the feedthrough housing 535) may be made of Inconel 625, Hastelloy C-276 (also $H_2S$ resistant), Tungsten, Molybdenum, Platinum, or any suitable conductive material. In FIGS. 6A and 6B, the lateral center-conductors 510 and 510' of the feedthrough connector 500, 500' may be made of beryllium copper with or without gold plating, or the like. Their dielectric insulators 515 and 515' may be made of PTFE, microporous PTFE, or the like.

In FIGS. 5A and 5B, a holding gland 545 may engage the (inner) thread 415 to couple the feedthrough connector 500 with the inner body of the probe 400, 400'. Tightening the holding gland 545 against the feedthrough flange 534 via a sliding washer 540 and against an O-ring 525 will seal the feedthrough connector 500, 500' with the probe 400, 400'. The probe body 420 may be coupled with the pipe wall by the use of the (outer) thread 415 on the probe body 420. Appropriately torqueing the probe body 420 at surface 417, which may be a hex cut or a flat cut, will seal it against the pipe wall by an O-ring 550. In some embodiments, the O-rings will be supported by a backup ring to increase sealing ability of the O-rings. The holding gland 545 will permit the passage of a microwave cable with a QMA connector (or other type of RF connector) to mate with the feedthrough QMA connector 536. A microwave cable gland (not shown) may be coupled with the inner thread 560 of the holding gland 545 to secure the microwave cable and make it dust- and weather-proof.

To reduce the number of coaxial interconnections in the feedthrough connector 500 (and hence to further minimize electrical insertion loss), the feedthrough first dielectric insulator 515 in FIG. 6A may be replaced with glass by extending the glass-metal seal 505 between insulator 530 and inner conductor 532 towards (and flush with) the feedthrough's first end 502. The extended glass-sealed center-conductor 532 (replacing the first lateral center-conductor 510) may be made flush with the surface at the first end 502, and designed to be electrically mate-able with the non-open-aperture end 403 of the inner conductor 432 of the probe's first integral pressure barrier made of glass-metal seal 405 (FIG. 4A) or of ceramic-metal seal 405' (FIG. 4B). Thus, an at least partially extended glass-seal 505 coaxial feedthrough connector 500 can be integrally coupled with a glass- or ceramic-sealed probe 400, 400' to provide a coaxial probe having a dual-pressure integral barrier design.

Similarly, the feedthrough second dielectric insulator 515' in FIG. 6A may also be replaced with glass by extending the glass-metal seal 505 between insulator 530 and center-conductor 532 towards the feedthrough's second end 504 (to fill the RF connector 536 housing, such as a QMA connector). The extended glass-sealed center-conductor 532 (replacing the second lateral center-conductor 510') may be made electrically mate-able with the QMA connector of a microwave cable (not shown). Thus, a partial or fully extended glass-seal coaxial feedthrough connector 500 can be integrally coupled with a glass- or ceramic-sealed probe 400, 400' to provide a coaxial probe having a dual-pressure integral barrier design.

Figure 6C:
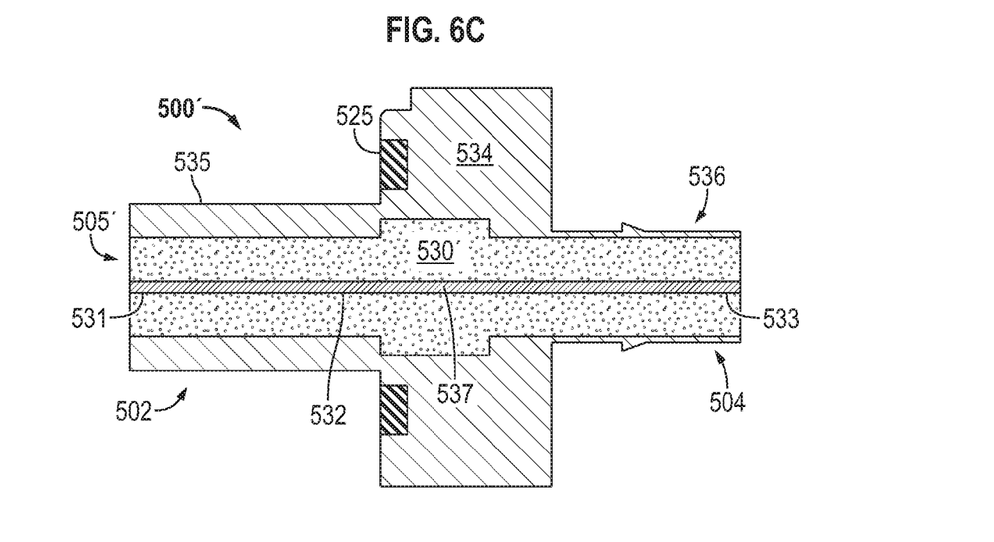

A fully extended ceramic-seal coaxial feedthrough connector 500' may be similarly made as shown in FIG. 6C. The feedthrough first dielectric insulator 515 in FIG. 6B may be replaced with ceramic by extending the ceramic-metal seal 505' between insulator 530' and center-conductor 532 towards (and flush with) the feedthrough's first end 502. The extended ceramic-sealed center-conductor 532 (replacing the first lateral center-conductor 510) may be made flush with the surface at the first end 502, and designed to be electrically mate-able with the non-open-aperture end 403 of the inner conductor 432 of the probe's first integral pressure barrier made of a ceramic-metal seal 405' (FIG. 4B), or of a glass-metal seal 405 (FIG. 4A). Thus, an at least partially extended ceramic-seal 505' coaxial feedthrough connector 500 can be integrally coupled with a glass- or ceramic-sealed probe 400, 400' to provide a coaxial probe having a dual-pressure integral barrier design.

With the use of a larger size RF connector 536 (such as an N-type connector shown in FIG. 3A), the feedthrough second dielectric insulator 515' in FIG. 6B may be replaced with ceramic by extending the ceramic-metal seal 505' between insulator 530' and center conductor 532 towards the feedthrough's second end 504 (to fill the larger connector 536 housing). The extended ceramic-sealed center-conductor 532 (replacing the second lateral center-conductor 510') may be made electrically mate-able with the N-type connector of a microwave cable (not shown). The feedthrough holding gland 545 may be redesigned to accommodate increased connector size. Hence, a partial or fully extended ceramic-seal 505' coaxial feedthrough connector 500' can be integrally coupled with a glass- or ceramic-sealed probe 400, 400' to provide a coaxial probe having a dual-pressure integral barrier design.

In some embodiments, a water conductivity probe 400 includes a coaxial probe body 420 having a front-aperture 410 in which an insulator 430 surrounds and is sealingly coupled with an inner-conductor 432, the inner-conductor 432 having a first end 401 and a second end 403. The insulator 430 is sealingly coupled with an inner portion of the coaxial probe body 420, such as aperture 410 to form a first integral pressure barrier. A coaxial feedthrough connector 500 is removably and sealingly coupled with a passageway 409 in the coaxial probe body. The connector 500 is positioned adjacent the insulator 430 and is electrically coupled with the inner-conductor 432 to form a second integral pressure barrier.

The coaxial feedthrough connector 500 may include a center-conductor 532 having a first end 531, a center section 537, and a second end 533 and a feedthrough insulator 530 surrounding and sealingly coupled with at least a portion of the center-conductor 532. A coaxial feedthrough connector housing 535 surrounds and is sealingly coupled with the feedthrough insulator 530 to form a second seal 505 between the center-conductor 532 and the coaxial feedthrough connector housing 535, the coaxial feedthrough connector housing 535 acting as an outer conductor, wherein the center-conductor 532 is electrically coupled with the inner conductor 432 of the first integral pressure barrier.

In some embodiments a water conductivity probe 400 includes a coaxial probe body 432 having a first integral pressure barrier and a second integral pressure barrier, wherein the second integral pressure barrier comprises a coaxial feedthrough connector 500. In some embodiments, the coaxial feedthrough connector 500 includes a center-conductor 532 having a first end 531, a center section 537, and a second end 533. A first dielectric insulator 515 is coupled to and surrounds at least a portion of the center-conductor 532 and a first lateral center-conductor 510. The first lateral center-conductor 510 is electrically coupled to an adjacent inner conductor 432 of the first integral pressure barrier comprising a first seal 405. A second seal 505, which may be a glass-metal 505 or ceramic-metal seal 505', hermetically surrounds and is sealingly coupled with the center section 537 of the center-conductor 532. The center-conductor 532 is electrically coupled at the first end 531 to the first lateral center-conductor 510 and at the second end 533 to a second lateral center-conductor 510'. A second dielectric insulator 515' is coupled to and surrounds at least a portion of the center-conductor 532 second end 533 and the second lateral center-conductor 510'. A coaxial feedthrough connector housing 535 surrounds and is coupled with the first and second dielectric insulators 515, 515'. The connector housing 535 sealingly surrounds and is coupled with the second seal 505, wherein the coaxial feedthrough connector housing 535 serves as an outer conductor.

Figure 7:
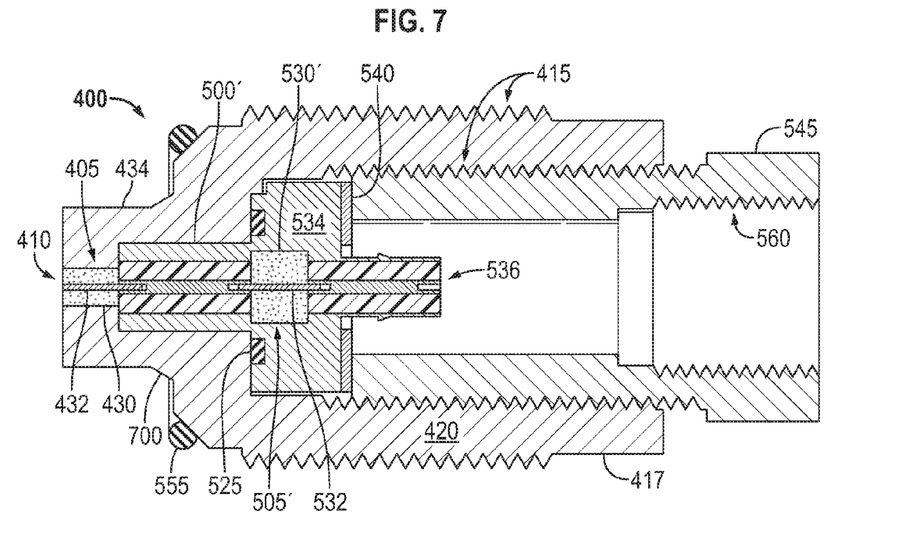
FIG. 7 shows a cross-sectional view of an electromagnetic sensor with integral pressure-containing coaxial feedthrough connector as a second pressure barrier, with autoclave metal-to-metal sealing surface and triangular O-ring seals with the pipe wall, according to some embodiments of the disclosure.

In some embodiments as illustrated in FIG. 7 for probe 400 with glass-metal seal 405 and feedthrough 500' with ceramic-metal seal 505', an autoclave sealing surface 700 is provided along the probe body 420 which may provide another metal to metal sealing surface, so that O-rings 550 and O-ring groove 550' may not be used to seal between the pipe wall and the probe body 420. Triangular O-ring seals 555 may also be used to provide an additional sealing area between a side portion of the probe body 420 and the pipe wall to which the probe is mounted. The probe 400 may include outer and inner threads 415 for coupling with the pipe and with the probe's feedthrough connector 500' by the use of holding gland 545. The outer threads 415 may not be process wetted. A flat cut forming surface 417 may be used to torque the probe when mounting it on the pipe wall of the blind-tee. The holding gland 545 will permit the passage of a microwave cable with a QMA connector or the like (not shown) to mate with the feedthrough QMA connector 536. A microwave cable gland (not shown) may be coupled with the inner thread 560 of the holding gland 545 to secure the microwave cable and make it dust- and weather-proof.

The interchangeability design of this disclosure permits that a feedthrough connector having a second integral pressure barrier having a glass-metal or a ceramic-metal seal be used with a probe having a first integral pressure barrier having a glass-metal or a ceramic-metal seal, as shown in FIG. 7. A probe having a ceramic-metal seal as the first integral pressure barrier may be used as it is more chemically resistant to oilfield treatment or stimulation fluids containing hydrofluoric acid.

The length of the probe 400 may be reduced as much as possible to minimize feedthrough center-conductor 510, 510' and inner conductor 532 length and hence to reduce electrical insertion loss, thermal-induced phase drift, and the associated machining cost of the probe body 420 and the long center-conductors 510, 510' and inner conductor 532. The compact dual-pressure integral barrier probe design may use a short microwave feedthrough and a phase-stable, weather-proof microwave cable to connect to the microwave electronics. The dual pressure barrier probe may have less sensitivity to the phase-shift change in a microwave cable caused by the undesirable thermal- or aging-induced dielectric-constant change than a probe with relatively long microwave cable connecting to its measurement electronics. Additionally, the size and cost of the sensing electronics Ex-d enclosure for use with the water-conductivity probe(s) that have integral second pressure barrier can be markedly reduced.

Although the preceding description has been described herein with reference to particular means, materials and embodiments, it is not intended to be limited to the particulars disclosed herein; rather, it extends to all functionally equivalent structures, methods, and uses, such as are within the scope of the appended claims.

The invention claimed is:

1. An electromagnetic sensor for multiphase flow measurement, comprising:
   a coaxial probe body having a passageway;
   a first integral pressure barrier coupled to at least a portion of the passageway, the first integral pressure barrier having a desired characteristic impedance; and
   a second integral pressure barrier coupled to at least another portion of the passageway, the second integral pressure barrier having a desired characteristic impedance.

2. The electromagnetic sensor of claim 1, wherein the first integral pressure barrier comprises:
   an inner conductor having a first end and a second end;
   an insulator surrounding and sealingly coupled with at least a portion of the inner conductor; and
   a portion of the passageway surrounding and sealingly coupled with the insulator to form a first seal between the inner conductor and the coaxial probe body, the coaxial probe body acting as an outer conductor, wherein the first end of the inner conductor and the insulator is flush with an open-aperture surface of the coaxial probe body.

3. The electromagnetic sensor of claim 2, wherein the insulator comprises a glass or a ceramic insulator such that the first seal has a glass-metal or a ceramic-metal seal between the inner conductor and the coaxial probe body.

4. The electromagnetic sensor of claim 2, wherein the second pressure barrier comprises a coaxial feedthrough connector coupled with the passageway.

5. The electromagnetic sensor of claim 4, wherein the coaxial feedthrough connector comprises:
   a center-conductor having a first end, a center section, and a second end;
   a feedthrough insulator surrounding and sealingly coupled with at least a portion of the center-conductor;

a coaxial feedthrough connector housing surrounding and sealingly coupled with the feedthrough insulator to form a second seal between the center-conductor and the coaxial feedthrough connector housing, the coaxial feedthrough connector housing acting as an outer conductor, wherein the center-conductor is electrically coupled with the inner conductor of the first integral pressure barrier.

6. The electromagnetic sensor of claim 5, wherein the coaxial feedthrough connector housing further comprises an RF connector.

7. The electromagnetic sensor of claim 6, further comprising:
a first lateral center-conductor having a first end and a second end, wherein the first lateral center-conductor first end is electrically coupled to the inner-conductor of the first integral pressure barrier and the first lateral center-conductor second end is electrically coupled to the center-conductor of the second pressure barrier; and
a first dielectric insulator coupled to and surrounding at least a portion of the first lateral center-conductor.

8. The coaxial feedthrough connector of claim 7, further comprising:
a second lateral center-conductor having a first end and a second end, wherein the second lateral center-conductor first end is electrically coupled to the center-conductor of the second integral pressure barrier and positioned adjacent the RF connector; and
a second dielectric insulator coupled to and surrounding at least a portion of the second lateral center-conductor.

9. The electromagnetic sensor of claim 4, wherein the coaxial feedthrough connector is coupled with the passageway using a sliding washer, an O-ring, and a coaxial feedthrough holding gland.

10. The electromagnetic sensor of claim 4, wherein the coaxial probe body has an autoclave metal to metal sealing surface.

11. A water conductivity probe, comprising:
a coaxial probe body having a front-aperture in which an insulator surrounds and is sealingly coupled with an inner-conductor, the inner-conductor having a first end and a second end, and further is sealingly coupled with an inner portion of the coaxial probe body to form a first seal comprising a first integral pressure barrier; and
an interchangeable second integral pressure barrier having a desired characteristic impedance.

12. The water conductivity probe of claim 11, wherein the interchangeable second integral pressure barrier comprises:
a coaxial feedthrough connector removably and sealingly coupled with a passageway in the coaxial probe body, positioned adjacent the insulator, and electrically coupled with the inner-conductor to form a second integral pressure barrier.

13. The water conductivity probe of claim 12, wherein the coaxial feedthrough connector comprises:

a center-conductor having a first end, a center section, and a second end;
a feedthrough insulator surrounding and sealingly coupled with at least a portion of the center-conductor;
a coaxial feedthrough connector housing surrounding and sealingly coupled with the feedthrough insulator to form a second seal between the center-conductor and the coaxial feedthrough connector housing, the coaxial feedthrough connector housing acting as an outer conductor, wherein the center-conductor is electrically coupled with the inner conductor of the first integral pressure barrier.

14. The water conductivity probe of claim 13, wherein the coaxial feedthrough connector housing further comprises an RF connector.

15. A water conductivity probe, comprising:
a coaxial probe body having a first integral pressure barrier and an interchangeable second integral pressure barrier.

16. The water conductivity probe of claim 15, wherein the first and second integral pressure barriers have a maximum allowable working pressure in the range of 5 kpsi to 20 kpsi.

17. The water conductivity probe of claim 16, wherein the maximum allowable working pressure is 15 kpsi.

18. The water conductivity probe of claim 15, wherein the second pressure barrier comprises a coaxial feedthrough connector.

19. The water conductivity probe of claim 18, wherein the coaxial feedthrough connector comprises:
a center-conductor having a first end, a center section, and a second end;
a first dielectric insulator coupled to and surrounding at least a portion of the center-conductor and a first lateral center-conductor, wherein the first lateral center-conductor is electrically coupled to an adjacent inner conductor of the first integral pressure barrier comprising a first seal;
a second seal having a glass-metal or ceramic-metal seal, the second seal hermetically surrounding and sealingly coupled with the center section of the center-conductor, wherein the center-conductor is electrically coupled at the first end to the first lateral center-conductor and at the second end to a second lateral center-conductor;
a second dielectric insulator coupled to and surrounding at least a portion of the center-conductor second end and the second lateral center-conductor; and
a coaxial feedthrough connector housing surrounding and coupled with the first and second dielectric insulator and sealingly surrounding and coupled with the second seal, wherein the coaxial feedthrough connector housing serves as an outer conductor.

20. The water conductivity probe of claim 19, wherein the coaxial feedthrough connector housing further comprises an RF connector.

* * * * *